United States Patent [19]
Moszner et al.

[11] Patent Number: 5,985,958
[45] Date of Patent: *Nov. 16, 1999

[54] LIGHT-CURING COMPOSITE MATERIAL

[75] Inventors: Norbert Moszner, Eschen; Volker Rheinberger, Vaduz, both of Liechtenstein

[73] Assignee: Ivoclar AG, Liechtenstein

[ * ] Notice: This patent issued on a continued prosecution application filed under 37 CFR 1.53(d), and is subject to the twenty year patent term provisions of 35 U.S.C. 154(a)(2).

[21] Appl. No.: 09/134,023

[22] Filed: Aug. 14, 1998

Related U.S. Application Data

[63] Continuation of application No. 08/780,968, Jan. 9, 1997, Pat. No. 5,847,025.

[30] Foreign Application Priority Data

Jan. 12, 1996 [DE] Germany .......................... 196 01 924

[51] Int. Cl.$^6$ ................ C08K 5/46; C08K 5/34; C08K 3/18; C08K 3/40
[52] U.S. Cl. .............. 524/83; 524/99; 524/430; 524/494; 524/718; 252/402; 252/403
[58] Field of Search ................ 523/116; 524/83, 524/99, 430, 494, 718; 252/402, 403

[56] References Cited

U.S. PATENT DOCUMENTS

| | | | |
|---|---|---|---|
| 4,279,986 | 7/1981 | Ohnishi et al. | 430/280 |
| 4,897,436 | 1/1990 | Buysch et al. | 524/83 |
| 5,059,643 | 10/1991 | Buysch et al. | 524/83 |
| 5,229,244 | 7/1993 | Hertler et al. | 430/176 |
| 5,401,815 | 3/1995 | Shimizu et al. | 526/62 |
| 5,503,759 | 4/1996 | Evans et al. | 252/47.5 |

FOREIGN PATENT DOCUMENTS

3821091 A1   1/1989   Germany .

OTHER PUBLICATIONS

L. Levy, "Inhibition of Acrylic Acid Polymerization by Phenothiazine and p–Methoxyphenol. II. Catalytic Inhibition by Phenothiazine," *Journal of Polymer Science: Part A: Polymer Chemistry*, 30:569–76 (1992).

*Primary Examiner*—Kriellion Sanders
*Attorney, Agent, or Firm*—Nixon, Hargrave, Devans & Doyle LLP

[57] ABSTRACT

A light-curing composite material is described which is characterized by a content of anaerobic stabilizer and/or stable organic radicals and which has a reduced light sensitivity and an improved vacuum stability and is therefore suitable in particular as a dental filling material.

14 Claims, No Drawings

LIGHT-CURING COMPOSITE MATERIAL

This is a continuation of U.S. application Ser. No. 08/780,968 filed Jan. 9, 1997, now U.S. Pat. No. 5,847,025.

The invention relates to a light-curing composite material which, owing to a content of special polymerization inhibitors, exhibits a reduced light sensitivity and an improved stability with respect to premature polymerization on deaeration, e.g. by applying below-atmospheric pressure. Furthermore, the invention also relates to the use of the composite material and to moulded dental products.

Light-curing composite materials are compositions which contain light-curing monomers and additionally fillers and optionally further additives. Light-curing composite materials used in the dental field are single-component systems which are characterized by a quick curing as a result of polymerization, good stability on storage, slight discoloration by the polymerization initiator system used and very low porosity after curing. Unlike cold-curing composite materials, light-curing composites are widely used in the dental field predominantly as filling composites or cements (see P. Riethe, Caries prevention and preservative therapy, in "Farbatlanten der Zahnmedizin", volume 6, page 190, G. Thieme Verlag, Stuttgart-New York, 1994). In order to stabilize light-curable dental filling composites, i.e. to prevent the premature polymerization of these materials, so-called stabilizers, in particular substituted phenols, e.g. 2,6-di-tert-butyl-4-methylphenol (BHT) or hydroquinone monomethyl ether (MEHQ), are added to them (see J. Viohl et al., Die Chemie zahnärztlicher Füllungskunststoffe, C. Hanser Verlag, Munich-Vienna 1986, page 27).

However, one disadvantage of the known light-curing dental composite materials, and in particular of the so-called hybrid composite materials, is that when they are handled, e.g. in the form of normally used pastes, there may be undesired premature curing as a result of intensive lighting or through sunlight (see P. Dionysopoulos, D. C. Watts, J. Oral Rehabil. 17 (1990) 9). Accordingly, the international standard for dental filling materials based on composites (ISO 4049: 1988) requires that these remain stable at an illuminance of about 10,000 lux for at least 60 seconds, i.e. that they do not cure.

The light sensitivity of a dental composite material is conventionally controlled by suitable matching of the composition and concentration of the photoinitiator used as well as by a specific selection of the filler components used. A reduction in light sensitivity by increasing the concentration of the stabilizers used does not generally achieve this object. This is probably due to the fact that the phenolic compounds usually used as stabilizers, such as MEHQ, are so-called aerobic stabilizers which are active only in conjunction with oxygen dissolved in the composite material, and which inhibit the growth of the polymer radicals via peroxyradicals formed with the oxygen (see J. J. Kurland, J. Polym. Sci., Polym. Chem. Ed. 18 (1980) 1139). However, since the saturation concentration of oxygen in most of the monomers used in the composite materials is in the region of less than 100 ppm, a concentration of conventional stabilizer markedly higher than this does not lead to a substantial reduction in light sensitivity (see M. J. Fried, Farbe und Lack 100 (1994) 604).

In addition to the problems connected with too high a light sensitivity, dental filling composites can also be adversely affected as regards their mechanical properties by inclusions of air and porosities resulting therefrom, which occur when the composite materials are being processed as is usual in the form of pastes. In order to improve the material properties of the composite material pastes, they are therefore generally deaerated in vacuo after their production. This deaeration can, however, lead to an uncontrolled polymerization and consequently to a premature curing and impairment of the properties of the composite materials. The premature curing is to be attributed to the fact that, as a result of the deaeration, the oxygen concentration in the composite pastes is reduced and hence also the effectiveness of the normally used aerobic stabilizers is reduced.

In addition to the conventional aerobic stabilizers, substances are also known which can effectively inhibit radical vinyl polymerization even in the absence of oxygen, and which are therefore called anaerobic stabilizers. Such an anaerobic stabilizer is e.g. phenothiazine which unlike MEHQ can inhibit the polymerization of acrylic acid even in the absence of oxygen (see L. B. Levy, J. Polym. Sci., Part A, Polym. Chem. 30 (1992) 569). Finally, so-called stable organic radicals are also described in the literature which can be used as polymerization inhibitors. Examples of such stable organic radicals are the 2,2-diphenyl-1-picrylhydrazyl (DPPH) radical, the galvinoxyl radical, the triphenylmethyl radical and the 2,2,6,6-tetramethylpiperidinyl-1-oxyl radical (see E. S. Gould, Mechanismus und Struktur in der organischen Chemie, Verlag Chemie, Weinheim, 1962, page 816).

Since both anaerobic stabilizers and stable organic radicals are very effective radical scavengers, it is to be expected that their incorporation in composite materials brings about only incomplete curing which would be very disadvantageous as a marked deterioration in the mechanical properties of the cured material would accompany it.

It is accordingly an object of the present invention to provide a light-curing composite material which is not polymerized prematurely on deaeration and the light sensitivity of which is controlled in such a way that polymerization induced by daylight is inhibited, but polymerization induced by light in the wavelength range of 400–550 nm is not impeded and therefore a substantial deterioration in the mechanical properties of the cured composite material is avoided.

This object is achieved by means of the light-curing composite material according to the present invention. The invention also relates to the use of the composite material, as well as to the moulded dental product.

The light-curing composite material according to the invention is characterized in that it contains (a) at least one light-curing monomer, (b) at least one filler and (c) at least one anaerobic stabilizer and/or stable organic radicals.

Anaerobic stabilizers are those compounds which are able to inhibit radical vinyl polymerization even in the absence of oxygen. These anaerobic stabilizers are preferably included in the composite material according to the invention in a quantity of 0.001 to 1.0, in particular 0.001 to 0.50 and particularly preferably 0.001 to 0.20% by weight.

Particularly advantageous anaerobic stabilizers are phenothiazine and/or the derivatives of phenothiazine corresponding to the following formula I

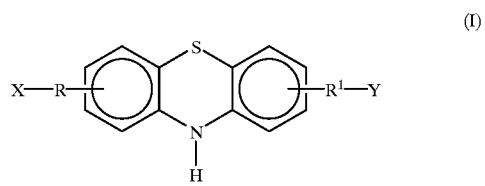

in which R, $R^1$, X, Y, $R^2$, $R^3$, $R^4$, $R^5$, $R^6$ and $R^7$, independently of each other, have the following meanings:

R and $R^1$=$C_1$ to $C_5$ alkylene or $C_1$ to $C_5$ oxyalkylene or $C_6$ to $C_{12}$ arylene X and Y=H, halogen, $NO_2$, $NH_2$, $NR^2R^3$, OH, $OR^4$, CN, CHO, CO—$R^5$, COOH, CO—$NH_2$, CO—$OR^6$, $CH_2$—CH=, $CH_2$=CH—CO—, $CH_2$=C($CH_3$)—CO—, SH or S—$R^7$ $R^2$ to $R^7$=alkyl, alkenyl, aryl, alkylaryl or arylalkyl having in each case 1 to 12 C atoms.

The composite material according to the invention can contain so-called stable organic radicals in place of or in addition to the anaerobic stabilizers. Stable organic radicals are taken to mean those organic radicals which, in a solid state or in solution, have a half-life of at least 30 days, in particular at least 12 months, at room temperature. As is known, (see H. A. Staab, Einführung in die theoretische organische Chemie, Verlag Chemie, Weinheim 1966, page 442 et seq.), radical stability in this case is caused above all by the mesomeric stabilization of the radicals or the destabilization of the corresponding dimeric combination products by steric effects. Stable carbon radicals, such as tribiphenylmethyl radicals, stable oxygen radicals such as galvinoxyl radicals or stable nitrogen radicals such as DPPH radicals are known inter alia.

The stable organic radicals are typically included in the composite material according to the invention in a quantity of 0.001 to 1.0, in particular 0.001 to 0.50 and particularly preferably 0.001 to 0.20% by weight.

2,2-Diphenyl-1-picrylhydrazyl (DPPH) radicals, galvinoxyl radicals and/or triphenylmethyl radicals are preferably used as stable organic radicals. However, 2,2,6,6-tetramethylpiperidinyl-1-oxyl radicals (TEMPO) or derivatives of TEMPO of the formulae (II) and (III) below are particularly preferably included in the materials according to the invention.

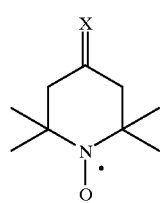

(II)

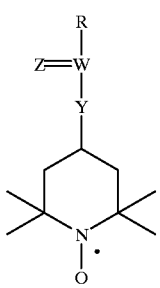

(III)

in which X, Y, Z, W and R, independently of each other, have the following meanings:

X=O or S

Y and Z=O, S or not present

W=C or not present

R=H or alkyl, alkenyl, aryl, alkylaryl or arylalkyl having in each case 1 to 12 C atoms.

The setting of the light sensitivity and stability on deaeration, also called vacuum stability, which are desired in each case in the composite materials, is carried out by a suitable choice of the quantity and type of anaerobic stabilizer and/or of the stable organic radicals. It has been shown in particular that even very small quantities of anaerobic stabilizer and/or stable organic radicals effectively prevent the undesired polymerization induced by daylight of the composite materials, without polymerization triggered by blue light (wavelength 400 to 550 nm) simultaneously being impeded. The latter is presumably also the reason for the fact that the use of the polymerization inhibitors provided according to the invention does not lead to a substantial deterioration in the mechanical properties of the cured material. Thus, both in the case of bending strength and in the case of flexural E-modulus, the cured material displays no substantial reductions in comparison with a material containing no anaerobic stabilizer and/or stable organic radicals.

In order to achieve the normal storage stability, the composite material according to the invention preferably also contains conventional polymerization inhibitors. Examples of such conventional polymerization inhibitors are 2,6-di-tert-butyl-4-methylphenol (BHT) and hydroquinone monomethyl ether (MEHQ). Typically the conventional polymerization inhibitors are included in the composite material in a quantity of up to 1.0% by weight.

It has been shown that the use of conventional polymerization inhibitors alone, even in relatively large quantities, did not lead to a substantial reduction in the light sensitivity or to an improvement in the vacuum stability of composite pastes. This was achieved only by means of the anaerobic stabilizer and/or the stable organic radicals.

The composite material according to the invention moreover contains at least one light-curing monomer. Ethylenically unsaturated monomers and in particular monofunctional or polyfunctional acrylates and/or methacrylates are preferably used for this purpose. Preferred examples of these are methyl (meth)acrylate, isobutyl (meth)acrylate, cyclohexyl (meth)acrylate, tetraethylene glycol di(meth)acrylate, diethylene glycol di(meth)acrylate, ethylene glycol di(meth)acrylate, polyethylene glycol di(meth)acrylate, butanediol di(meth)acrylate, hexanediol di(meth)acrylate, decanediol di(meth)acrylate, dodecanediol di(meth)acrylate, bisphenol-A-di(meth)acrylate, trimethylolpropane tri(meth)acrylate, as well as the products of the reaction of isocyanates, in particular di- and/or triisocyanates, with methacrylates containing OH groups. Examples of the last-mentioned products are the products obtained by reaction of 1 mole of hexamethylene diisocyanate with 2 moles of 2-hydroxyethylene methacrylate and of 1 mole of tri-(6-isocyanatohexyl)biuret with 3 moles of 2-hydroxyethyl methacrylate. Triethylene glycol di(meth)acrylate, 2,2-bis-4-(3-methacryloxy-2-hydroxypropoxy)-phenylpropane (Bis-GMA) and the products obtained by reaction of 1 mole of 2,2,4-trimethylhexamethylene diisocyanate with 2 moles of 2-hydroxyethyl methacrylate are particularly preferred.

The total quantity of light-curing monomers in the composite material according to the invention is preferably 7 to 80, particularly preferably 14 to 50, % by weight.

Furthermore the composite material according to the invention contains at least one filler. Particularly suitable fillers are inorganic fillers and in particular quartz powder or glass ceramic powder, aluminium oxides, mixed oxides such as $SiO_2$—$ZrO_2$ mixed oxide, or X-ray opaque fillers such as ytterbium trifluoride. Particularly preferred fillers are glass powder, e.g. barium glass, barium silicate glass, Li- or Al-silicate glass powders and finely divided silicas such as pyrogenic or precipitated silicas.

The fillers are preferably used in the composite material according to the invention in a quantity of 10 to 90, in particular 48 to 85, % by weight.

Furthermore the composite material preferably also contains initiators for photopolymerization, such as benzophenone, benzoin or derivatives thereof. Preferred photoinitiators are the α-diketones, such as 9,10-phenanthrene quinone, diacetyl, furil, anisil, 4,4'-dichlorobenzil and 4,4'-dialkoxybenzil. Camphorquinone is particularly preferably used. The photoinitiators are typically used in combination with an amine as activator, e.g. N,N-dimethyl-p-toluidine, N,N-dihydroxy-ethyl-p-toluidine and in particular N-(2-cyanoethyl)-N-methylaniline.

Finally, the composite material according to the invention can also contain conventional additives and especially in the case of dental composite materials additives such as dyes, pigments, plasticizers, lubricants, rheology modifiers or UV stabilizers.

In order to prepare the light-curing composite material according to the invention, the processes conventional in the preparation of dental composite materials are used, in which the stabilizers necessary according to the invention, namely the anaerobic stabilizer and/or the stable organic radicals, are incorporated into the composite material at any time during the preparation process, e.g. by simple mixing.

The composite material according to the invention is characterized in particular by the fact that, by containing small amounts of anaerobic stabilizer and/or stable organic radicals, its light sensitivity is controlled in such a way that it does not polymerize prematurely either on deaeration, e.g. by applying a vacuum, or when illuminated by means of daylight. Both the vacuum stability and the light sensitivity can be controlled simply by the type and quantity of anaerobic stabilizer and/or stable organic radicals.

The above properties make the composite material according to the invention in particular suitable as a dental filling material. It is, however, also possible to use it in the field of prosthesis, e.g. as a material for preparing crowns or bridges. The reduced sensitivity to daylight proves to be particularly advantageous here since the dental technician can carry out the modelling of e.g. a crown or bridge structure even in normal diffuse daylight, without this resulting in a premature polymerization.

The invention also relates to the use of the composite material as a dental material and in particular the use of the anaerobic stabilizer and/or the stable organic radicals to reduce the light sensitivity of the dental material and to inhibit the premature polymerization of the dental material on deaeration.

Finally, the invention also relates to a dental product moulded from the composite material according to the invention, in particular a filling, a crown or a bridge, which contains the composite material in at least partially cured form. The moulding of the composite material takes place in a manner known per se.

The invention is explained in more detail below with reference to examples.

EXAMPLES

Example 1

A monomer mixture was prepared first from the following substances:

| monomers: | bisphenol-A-glycidylmethacrylate (Bis-GMA)<br>urethane dimethacrylate (UDMA), prepared from 1 mole of 2,2,4-trimethylhexamethylene diisocyanate and 2 moles of 2-hydroxyethyl methacrylate<br>triethylene glycol dimethacrylate (TEGDMA) |
|---|---|
| photoinitiators: | combination of camphorquinone (CC) and N-(2-cyanoethyl)-N-methylaniline (CEMA) |
| inhibitor: | hydroquinone monomethyl ether (MEHQ) |

The monomer mixture had the following composition:

| Component | % by weight |
|---|---|
| Bis-GMA | 41.77 |
| UDMA | 37.42 |
| TEGDMA | 20.00 |
| MEHQ | 0.01 |
| CC | 0.30 |
| CEMA | 0.50 |

This monomer mixture was then mixed with fillers in order to prepare a composite material with the following composition:

| % by weight | Component |
|---|---|
| 26.0 | monomer mixture |
| 44.0 | silanized barium aluminium silicate glass (glass filler, from Schott glass works) |
| 14.5 | ytterbium trifluoride (Rhone-Poulenc) |
| 14.5 | silanized spherical $SiO_2$—$ZrO_2$ mixed oxide (Spharosil, Tokyamo Soda) |
| 1.0 | silanized pyrogenic silicic acid (Ox-50, Degussa) |

Small quantities of phenothiazine as anaerobic stabilizer or 2,2,6,6-tetramethylpiperidinyl-1-oxyl radicals (TEMPO) or 2,2-diphenyl-1-picrylhydrazyl radicals (DPPH) as stable organic radicals were then added to this composite material. The stated quantities relate to the quantity of composite material used without phenothiazine, TEMPO and DPPH. In tests of the obtained composite material with added phenothiazine or TEMPO or DPPH and, for comparison, those without these additives, the light sensitivity, the bending strength and the flexural E-modulus were then determined according to ISO 4049. The measured values are listed below.

| Additive (% by weight) | Light sensitivity (s) | Bending strength (MPa) | Flexural E-modulus (GPa) |
|---|---|---|---|
| without Phenothiazine | 70 | 114 | 9.5 |
| 0.03 | 95 | 111 | 9.5 |
| 0.05 | 105 | 121 | 10.9 |
| 0.10 | 130 | 110 | 9.5 |
| TEMPO | | | |
| 0.0025 | 105 | 117 | 9.5 |
| 0.005 | 150 | 121 | 9.5 |
| 0.01 | 240 | 124 | 9.4 |

| Additive (% by weight) | Light sensitivity (s) | Bending strength (MPa) | Flexural E-modulus (GPa) |
|---|---|---|---|
| DPPH | | | |
| 0.10 | 145 | 124 | 11.6 |

The results show that the light sensitivity of the composites can be markedly reduced by addition of phenothiazine or TEMPO or DPPH, without this leading to a deterioration in the mechanical properties of the materials.

Since curing took place in all cases under the same conditions with light of the wavelength 400–550 nm, the above values for bending strength and flexural E-modulus also prove that hindrance of light curing does not occur in the case of the composite materials according to the invention even though they contain anaerobic stabilizer or stable organic radicals.

Example 2

A composite material of the following composition was prepared analogously to Example 1:

| % by weight | Component |
|---|---|
| 19.0 | monomer mixture according to Example 1 |
| 51.0 | silanized barium aluminium silicate glass (glass filler) |
| 14.5 | ytterbium trifluoride |
| 14.5 | silanized spherical $SiO_2$—$ZrO_2$ mixed oxide (Spharosil) |
| 1.0 | silanized pyrogenic silicic acid (Ox-50) |

The paste obtained was deaerated in a kneading machine at <50 mbar. The paste then began to polymerize after about 5 minutes.

A paste of the same composition but with an addition of 0.06% by weight of phenothiazine (relative to the quantity of paste prior to the addition of phenothiazine) was on the other hand stable for 20 minutes, which is sufficient for a complete deaeration.

In the case of a paste of the same composition but with an addition of 0.005% by weight of TEMPO instead of phenothiazine (relative to the quantity of paste prior to the addition of (TEMPO), no signs of polymerization were visible even after 1 hour.

We claim:

1. A light-curing, polymerizable composite material, comprising:

(a) at least one light-curing monomer,
   (b) at least one filler, and
   (c) at least one anaerobic stabilizer, at least one stable organic radical, or mixtures of at least one anaerobic stabilizer and at least one stable organic radical.

2. The composite material according to claim 1, wherein the anaerobic stabilizer is a phenothiazine or a derivative thereof of the following formula I

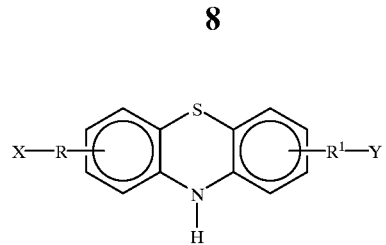

in which R, $R^1$, X, Y, $R^2$, $R^3$, $R^4$, $R^5$, $R^6$ and $R^7$, independently of each other, have the following meanings:
   R and $R^1$=$C_1$ to $C_5$ alkylene or $C_6$ to $C_5$ oxyalkylene or $C_6$ to $C_{12}$ arylene
   X and Y=H, halogen, $NO_2$, $NH_2NR^2R^3$, OH, $OR^4$, CN, CHO, CO—$R^5$, COOH, CO—$NH_2$, CO—$OR^6$, $CH_2$=CH—, $CH_2$=CH—CO—, $CH_2$=C($CH_3$)—CO—, SH or S—$R^7$
   $R^2$ to $R^7$=alkyl, alkenyl, aryl, alkylaryl or arylalkyl having in each case 1 to 12 C atoms.

3. The composite material according to claim 1, wherein the composite material contains 0.001 to 1.0% by weight of the anaerobic stabilizer.

4. The composite material according to claim 1, wherein the stable organic radical is a radical selected from the group consisting of 2,2-diphenyl-1-picrylhydrazyl radicals, galvinoxyl radicals, triphenylmethyl radicals, radicals of the formula II, and radicals of the formula III

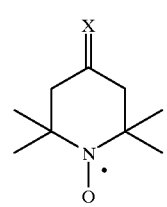

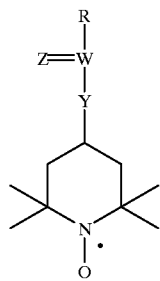

in which X, Y, Z, W and R, independently of each other, have the following meanings:
   X=O or S
   Y and Z=O, S or not present
   W=C or not present
   R=H or alkyl, alkenyl, aryl, alkylaryl or arylalkyl having in each case 1 to 12 C atoms.

5. The composite material according to claim 1, wherein the composite material contains 0.001 to 1.0% by weight of the stable organic radical.

6. The composite material according to claim 1 further comprising up to 1.0% by weight of a conventional polymerization inhibitor.

7. The composite material according to claim 1, wherein the composite material contains 7 to 80% by weight of the light-curing monomer.

8. The composite material according to claim 1, wherein the composite material contains 10 to 90% by weight of the filler.

9. The composite material according to claim 3, wherein the composite material contains 0.001 to 0.50% by weight of the anaerobic stabilizer.

10. The composite material according to claim 1, wherein the composite material contains 0.001 to 0.20% by weight of the anaerobic stabilizer.

11. The composite material according to claim 5, wherein the composite material contains 0.001 to 0.50% by weight of the stable organic radical.

12. The composite material according to claim 5, wherein the composite material contains 0.001 to 0.20% by weight of the stable organic radical.

13. The composite material according to claim 7, wherein the composite material contains 14 to 50% by weight of the light-curing monomer.

14. The composite material according to claim 8, wherein the composite material contains 48 to 85% by weight of the filler.

* * * * *